US010588578B2

(12) United States Patent
Beck

(10) Patent No.: US 10,588,578 B2
(45) Date of Patent: Mar. 17, 2020

(54) MR DATA ACQUISITION USING PHYSIOLOGICAL MONITORING

(75) Inventor: Gabrielle Marianne Beck, Venlo (NL)

(73) Assignee: Koninklijke Philips N.V., Eindhoven (NL)

(*) Notice: Subject to any disclaimer, the term of this patent is extended or adjusted under 35 U.S.C. 154(b) by 409 days.

(21) Appl. No.: 13/879,417

(22) PCT Filed: Oct. 12, 2011

(86) PCT No.: PCT/IB2011/054501
§ 371 (c)(1),
(2), (4) Date: Apr. 15, 2013

(87) PCT Pub. No.: WO2012/049634
PCT Pub. Date: Apr. 19, 2012

(65) Prior Publication Data
US 2013/0211236 A1 Aug. 15, 2013

(30) Foreign Application Priority Data
Oct. 14, 2010 (EP) .................................... 10187516

(51) Int. Cl.
A61B 5/00 (2006.01)
G01R 33/567 (2006.01)
(Continued)

(52) U.S. Cl.
CPC .......... A61B 5/7285 (2013.01); A61B 5/0037 (2013.01); A61B 5/055 (2013.01);
(Continued)

(58) Field of Classification Search
CPC ........................... A61B 5/7285; A61B 5/7296
(Continued)

(56) References Cited

U.S. PATENT DOCUMENTS 4,878,499 A 11/1989 Suzuki et al.
5,363,844 A * 11/1994 Riederer ............ G01R 33/5676
600/413
(Continued)

FOREIGN PATENT DOCUMENTS

CN 2768671 Y 4/2006
EP 1729144 A1 12/2006
(Continued)

OTHER PUBLICATIONS

Parkes, Breath holding and its breakpoint, Experimental Physiology, vol. 91, Issue 1 (Jan. 2006).*
(Continued)

Primary Examiner — Rajeev P Siripurapu

(57) ABSTRACT

Systems, devices and methods for performing a magnetic resonance imaging scan of a patient. For example, a method of performing a magnetic resonance imaging scan on a patient can include monitoring a physiological signal level of the patient, analyzing the monitored physiological signal level, and providing instructions to the patient and/or changing the environmental conditions exposed to the patient. The instructions and/or the change of the environmental conditions of the patient can be based on the monitored physiological signal level. The instructions can include an acoustic command and/or a visual command. The changing of the environmental conditions can include visual simulation, acoustic stimulation and/or air conditioning change.

10 Claims, 2 Drawing Sheets

(51) Int. Cl.
*A61B 5/055* (2006.01)
*G01R 33/563* (2006.01)

(52) U.S. Cl.
CPC ..... *G01R 33/5673* (2013.01); *G01R 33/5676* (2013.01); *G01R 33/56325* (2013.01); *G01R 33/56366* (2013.01)

(58) Field of Classification Search
USPC .................................. 600/410, 413, 418
See application file for complete search history.

(56) References Cited

U.S. PATENT DOCUMENTS

| | | | |
|---|---|---|---|
| 6,201,393 B1* | 3/2001 | Bernstein et al. ............ 324/309 |
| 7,182,083 B2 | 2/2007 | Yanof et al. | |
| 2002/0077538 A1* | 6/2002 | Saranathan et al. .......... 600/410 |
| 2005/0119650 A1 | 6/2005 | Sanders | |
| 2007/0172029 A1 | 7/2007 | Felmlee et al. | |
| 2008/0004518 A1 | 1/2008 | Stehning et al. | |
| 2008/0051261 A1* | 2/2008 | Lewis ............... A63B 22/0242 482/54 |
| 2008/0183475 A1 | 7/2008 | Hirota et al. | |
| 2009/0112083 A1 | 4/2009 | Aulbach et al. | |
| 2009/0192399 A1* | 7/2009 | Choi ................. A61B 5/02405 600/519 |
| 2009/0302840 A1* | 12/2009 | Fung et al. .................... 324/309 |
| 2010/0152600 A1* | 6/2010 | Droitcour ............... A61B 5/05 600/534 |
| 2010/0264924 A1* | 10/2010 | Stemmer ...................... 324/309 |

FOREIGN PATENT DOCUMENTS

| | | |
|---|---|---|
| JP | 2007003264 A | 1/2007 |
| JP | 2008148918 A | 7/2008 |

OTHER PUBLICATIONS

Keall, P.J. et al. "The management of respiratory motion in radiation oncology report of AAPM Task Group 76(a)". Med. Phys. 33(10), Oct. 2006, Am. Association of Physicists in Medicine, pp. 3874-3900.

Xing, L. et al. "Overview of image-guided radiation therapy". Medical Dosimetry, vol. 31, No. 2, pp. 91-112, 2006. American Association of Medical Dosimetrist.

Kini, Vijay R. et al "Patient Training in Respiratory-Gated Radiotherapy", Medical Dosimetry, vol. 28, No. 1, 2003, pp. 7-11.

Taylor, Andrew M. et al "Calculation of a Subject-Specific Adaptive Motion-Correction Factor for Improved Real-Time Navigator Echo-Gated Magnetic Resonance Coronary Angiography", Journal of Cardiovascular Magnetic Resonance, vol. 1, No. 2, 1999, pp. 131-138.

* cited by examiner

MR DATA ACQUISITION USING PHYSIOLOGICAL MONITORING

This application is a national stage application under U.S.C. § 371 of International Application No. PCT/IB2011/054501 filed on Oct. 12, 2011 and published in the English language on Apr. 19, 2012 as International Publication No. WO 2012/049634A1, which claims priority to European Application No. 101875169.9 filed on Oct. 14, 2010, the entire disclosures of which are incorporated herein by reference.

FIELD OF THE INVENTION

The invention relates to a method of performing magnetic resonance imaging scan of a patient, a computer program product and an MRI system.

BACKGROUND OF THE INVENTION

Image-forming MR methods, which utilize the interaction between magnetic field and nuclear spins in order to form two-dimensional or three-dimensional images are widely used nowadays, notably in the field of medical diagnostics, because for the imaging of soft tissue they are superior to other imaging methods in many respects, they do not require ionizing radiation, and they are usually not invasive. MRI is used for example as imaging technique to visualize myocardial injury. Cardiac and respiratory triggered MR imaging can be used to image morphology, time resolved cine movies may reveal cardiac function, dynamic contrast enhanced imaging can be utilized to measure perfusion and MR tagging sequences can be used to study the contraction of the myocardium in detail.

According to the MR method in general, the body of a patient or in general an object to be examined is arranged in a strong, uniform magnetic field BO whose direction at the same time defines an axis, normally the z-axis, of the coordinate system on which the measurement is based.

The magnetic field produces different energy levels for the individual nuclear spins in dependence on the applied magnetic field strength which spins can be excited (spin resonance) by application of an alternating electromagnetic field (RF field) of defined frequency, the so called Larmor frequency or MR frequency. From a macroscopic point of view the distribution of the individual nuclear spins produces an overall magnetization which can be deflected out of the state of equilibrium by application of an electromagnetic pulse of appropriate frequency (RF pulse) while the magnetic field extends perpendicularly to the z-axis, so that the magnetization performs a precessional motion about the z-axis.

Any variation of the magnetization can be detected by means of receiving RF antennas, which are arranged and oriented within an examination volume of the MR device in such a manner that the variation of the magnetization is measured in the direction perpendicularly to the z-axis.

In order to realize spatial resolution in the body, switching magnetic field gradients extending along the three main axes are superposed on the uniform magnetic field, leading to a linear spatial dependency of the spin resonance frequency. The signal picked up in the receiving antennas then contains components of different frequencies which can be associated with different locations in the body.

The signal data obtained via the receiving antennas corresponds to the spatial frequency domain and is called k-space data. The k-space data usually includes multiple lines acquired with different phase encoding. Each line is digitized by collecting a number of samples. A set of samples of k-space data is converted to an MR image, e.g. by means of Fourier transformation.

A major criterion for obtaining high quality MR images is to ensure that the imaged region of interest is not moving during an MR scan. In case of for example abdominal imaging this becomes a serious problem since physically necessary patient breathing and thus patient movement translates into blurring and ghosting of the acquired MR image. Consequently, a breath hold is required by the patient during the MR imaging scan in order to prevent any movement in the imaged region of interest.

U.S. Pat. No. 7,182,083 B2 discloses an integrated respiratory monitor and CT imaging device apparatus. The respiratory monitor system is adapted to engage a patient and generate a respiratory signal representative of a breath hold level of the patient during a breath hold. The imaging device is adapted to scan the patient during the breath hold and generate a volumetric image data set of the patient. The respiratory sensor and imaging device are operatively connected to associate the respiratory signal representative of the breath hold level of the patient together with the volumetric image data set of the patient.

Applying breath hold commands and starting an imaging scan when the patient has reached the breath hold state can introduce operator dependent variations. Breath hold sequences typically are started too early when the breath hold state has not been reached yet which translates into blurring and ghosting of the image. In the breath hold state, the breath hold may "drift away" also leading to motion related problems. Also automated breath hold commands are not patient dependent thus neglecting the capability to follow the breath hold commands and to address the overall patient situation. The patient's breath hold capabilities typically are related to the progress and the severity of a patient's disease.

SUMMARY OF THE INVENTION

From the foregoing it is readily appreciated that there is a need for an improved imaging method. It is consequently an object of the invention to provide an improved method for performing a magnetic resonance imaging scan in an optimized patient adapted manner.

In accordance with the invention, a method of performing a magnetic resonance imaging scan on a patient is provided, the method comprising monitoring a physiological signal level of the patient, analyzing the monitored physiological signal level and providing instructions to the patient and/or changing the environmental conditions exposed to the patient, wherein the instructions and/or changing of the environmental conditions are adapted to the monitored physiological signal level.

Embodiments of the invention have the advantage that with respect to the physiological situation of the patient the patient can dynamically be instructed to optimize behavior such that a respective MR imaging scan can be performed in an optimized manner, i.e. without motion-related problems like blurring and ghosting in the reconstructed MR image.

Consequently, the present invention uses automatic commands which are adapted to guide the patient to a good physiological condition and to take care that the patient stays in the condition. Additionally or alternatively the present invention dynamically changes the environmental conditions exposed to the patient in accordance with the monitored physiological signal level.

In accordance with an embodiment of the invention, the instructions comprise acoustic commands like voice commands and/or visual commands. In either case it is ensured that the patient can be instructed in an appropriate manner within the magnet bore with respect to a desired physiological condition.

In accordance with an embodiment of the invention, changing the environmental conditions of the patient comprises adapting visual and acoustic media exposed to the patient such that an in bore "Ambient Experience" changes. This also comprises changes in the air conditioning exposed to the patient. For example, air conditioning may be adapted in accordance with air humidity, oxygen level, nitrogen level, temperature and/or air flow through the magnet bore. In either case this permits to comfort the patient both physically and emotionally by dynamically reacting on perceived needs and physiological reactions of the patient. Thus, the environment within the magnet bore is personalized for actual patient's needs. A consequence is that patients can be easier motivated and/or can be distracted to achieve a desired stable physiological condition.

In accordance with a preferred embodiment of the invention, the physiological signal level comprises a breath hold level of the patient. However, generally the physiological signal level may comprise signal levels regarding breathing and/or body motion and/or cardiac activity of the patient.

In accordance with a further embodiment of the invention, the breath hold instructions comprise for example breath in and breath out command timings and/or 'stop breathing' or 'please hold' commands and/or hyperventilation commands and/or patient motivation commands for keeping the breath hold level and/or patient comfort commands.

The purpose of the above mentioned hyperventilation breath hold commands is that this enables for difficult breath holders to increase the breath hold time at a given breath hold level.

For example, in case of monitoring cardiac activities breathe in and breathe out command timings and patient comfort commands permit to achieve a desired level of cardiac activity.

These instructions are dynamically chosen adapted to the actually monitored physiological signal level and thus guide the patient's physiological behavior in a desired manner.

In an example, the timing of the breath in and breath out commands may be adapted to the actual breathing state while it is carefully checked if the commands are followed. In case that the breath hold state is reached, the automated breath hold command advises to 'stop breathing'. In case that a patient does not stop breathing, another automated short 'stop breathing' command may be given.

Patient motivation commands and/or in bore "Ambient Experience" changes psychologically motivate the patient to keep his actual breath hold level. For example, this may be performed by providing the patient information about a remaining required breath hold time or by visually stimulating the patient to suppress the upcoming breath reflex.

It has to be noted here that analyzing the monitored physiological signal level does not only include an analysis on the actual physiological signal level, but may also comprise analysis of motion-relevant statistics over a certain time span in order to obtain general information for example on the patient's breath hold capabilities or on the patients cardiac activities. Generally, for example the breathing history of the patient can be analyzed in order to determine the capability to hold the breath after an automatic breath hold command has been given including the breath hold lengths and drifts during a breath hold. This may also include an analysis on the capability to follow an issued breath hold command including response times but also possible free breathing characteristics such as non-moving periods in the end expiration/inspiration phase and the presence of an apnea. For example, in case a patient is re-scanned in another MR imaging scan, the motion history statistics previously acquired can be recovered from a previous study.

In case that from the motion-relevant statistics it is seen that the patient has difficulties holding the breath, patients can be motivated by mentioning the importance to hold the breath and indicating the remaining scan time. Visual stimulations can be provided with the remaining required breath hold time motivating the patient to further hold the breath. Also acknowledging the patient in case that the breath hold has been improved is a possibility to further motivate patients.

In accordance with a further embodiment of the invention, in case a predefined physiological signal level is not accomplished, the method further comprises optimizing the imaging protocol for performing a magnetic resonance imaging scan, wherein the optimization is adapted to the monitored physiological signal level. Here, an 'optimization' of the imaging protocol can be understood as triggering or gating of an MR scan at selected points in the respiratory cycle of the patient. It however also can be seen as a change in individual parameters of the MR imaging sequence or substitute the imaging sequence by a different imaging sequence.

In accordance with an embodiment of the invention, the optimization of the imaging protocol comprises calculating the expected maximum breath hold time within a predefined breath hold level of the patient and changing the actually selected imaging protocol to a new imaging protocol, the new imaging protocol requiring a respective data acquisition time for completion of a respective magnetic resonance imaging scan, wherein the new imaging protocol is chosen in accordance with the data acquisition time being shorter then or matching the calculated expected maximum breath hold time.

For example, in case it is expected that the patient can only hold his breath for 7 seconds, wherein an actually selected imaging protocol would require a breath hold of at least 15 seconds, this actually selected imaging protocol may be exchanged by a new imaging protocol which requires a data acquisition time of 7 seconds. The new imaging protocol may acquire the essential information in the first 7 seconds with the possibility to extend acquisition time in case that the patient can hold his breath longer successively improving image quality.

Generally, this concept may be extended to any kind of physiological signal level. For example, considering cardiac activity, the optimization of the imaging protocol may comprise calculating the expected heart rate and changing the actually selected imaging protocol to a new imaging protocol, the new imaging protocol requiring a respective data acquisition time for completion of a respective magnetic resonance imaging scan, wherein the new imaging protocol is chosen in accordance with the data acquisition time being shorter then or matching the calculated expected heart rate.

In accordance with an embodiment of the invention, the new imaging protocol may use centric k-space acquisition.

It has to be noted, that besides reducing the data acquisition time it is also possible to contrary increase the data acquisition time for example to enhance the resolution of the acquired MR images in case it is determined that the patient's capabilities for breath holding are better than expected.

In accordance with an embodiment of the invention, the optimization of the imaging protocol comprises extending the actually selected imaging protocol by applying a preliminary imaging protocol, the preliminary imaging protocol preceding the actually selected imaging protocol, wherein a preliminary magnetic resonance imaging scan is performed using the preliminary imaging protocol until the predefined physiological signal level is accomplished.

For example, in case that a 'stop breathing' command has been given and acquisition is started with the breath hold level still being drifting, acquisition points may be registered until a breath hold plateau with a specified breath hold level criterion is reached. These acquisition points can be re-acquired within the same breath hold and can be replaced to improve image quality. Another possibility is to not re-acquire but synthetically derive these k-space acquisition points using parallel imaging or compressed sensing methodologies.

In accordance with a further embodiment of the invention, the preliminary imaging protocol is optimized with respect to acoustically pretending that an imaging scan is running. Thus, the patient is assuming that a real imaging scan is already running which psychologically motivates him to put more efforts on holding the desired breath hold level or on stop moving his body or on letting the patient get used to the sudden change in gradient noise to get a stable heart activity.

In other words, the acoustic gradient noise may be adapted to change dependent on the cardiac or breathing motion which in turn influences the patient's behavior such as breathing and heart beat. Hence acoustically pretending continuous gradient noise helps to calm down the patient.

In accordance with a further embodiment of the invention, the new imaging protocol comprises the actually selected imaging protocol with instructions for an adapted image resolution, wherein the adapted image resolution results in the respective data acquisition time for completion of a magnetic resonance imaging scan. As mentioned above, this may be performed by adapting for example the way the k-space is sampled.

Alternatively or additionally to acoustically pretending an ongoing imaging scan by providing a preliminary imaging protocol it is also possible to acoustically emulate an ongoing imaging scan to the patient for example using loud speakers in case a predefined physiological signal level is not accomplished.

In accordance with a further embodiment of the invention, monitoring the breath hold level of the patient comprises repeatedly performing magnetic resonance navigator scans on the region of interest to be imaged during the magnetic resonance imaging scan, wherein the method further comprises during the navigator scans and/or the imaging scan to determine a physical movement within the region of interest from the navigator scans, wherein the movement results from a change in the patient's breath hold level, and adjusting the slice positions in accordance with the determined physical movement in order to compensate the acquired image data for the physical movement.

Thus, in case of the respiratory belt and the navigator acquisitions the breath hold can be continuously monitored. In case of navigator acquisitions this can be done by interleaving the navigator acquisition with the actual data acquisition. The advantage of the navigator acquisition is that in case the breath hold drifts, small drifts can thus be corrected by adapting the slice position (slice tracking) next to reminding the patient via an automatic command to 'further hold the breath'. Larger drifts or the capability not to hold the breath leads to acquisition points to be re-acquired later or derived synthetically.

It has to be noted that in case the motion control detects that a patient cannot follow the breath hold instructions and also cannot hold the breath for a specified time not fulfilling a specified breath capability criteria, the imaging protocols can be set up to be automatically changed within the exam to a specified free breathing or a short breath hold protocol with a lower quality (lower resolution, 2D etc). The consequence is that the 'recovery' period of the patient is extended.

In another aspect the invention relates to a computer program product comprising computer executable instructions to perform the method steps as described above.

In another aspect, the invention relates to a magnetic resonance imaging system for performing a magnetic resonance imaging scan for example during breath hold of a patient, the system being adapted for monitoring a physiological signal level of the patient, analyzing the monitored physiological signal level and providing instructions to the patient, wherein the instructions are adapted to the monitored breath hold level.

BRIEF DESCRIPTION OF THE DRAWINGS

The enclosed drawings disclose preferred embodiments of the invention. It should be understood, however, that the drawings are designed for the purpose of illustration only and not as a definition of the limits of the invention. In the drawings.

DETAILED DESCRIPTION OF THE EMBODIMENTS

Figure 1:
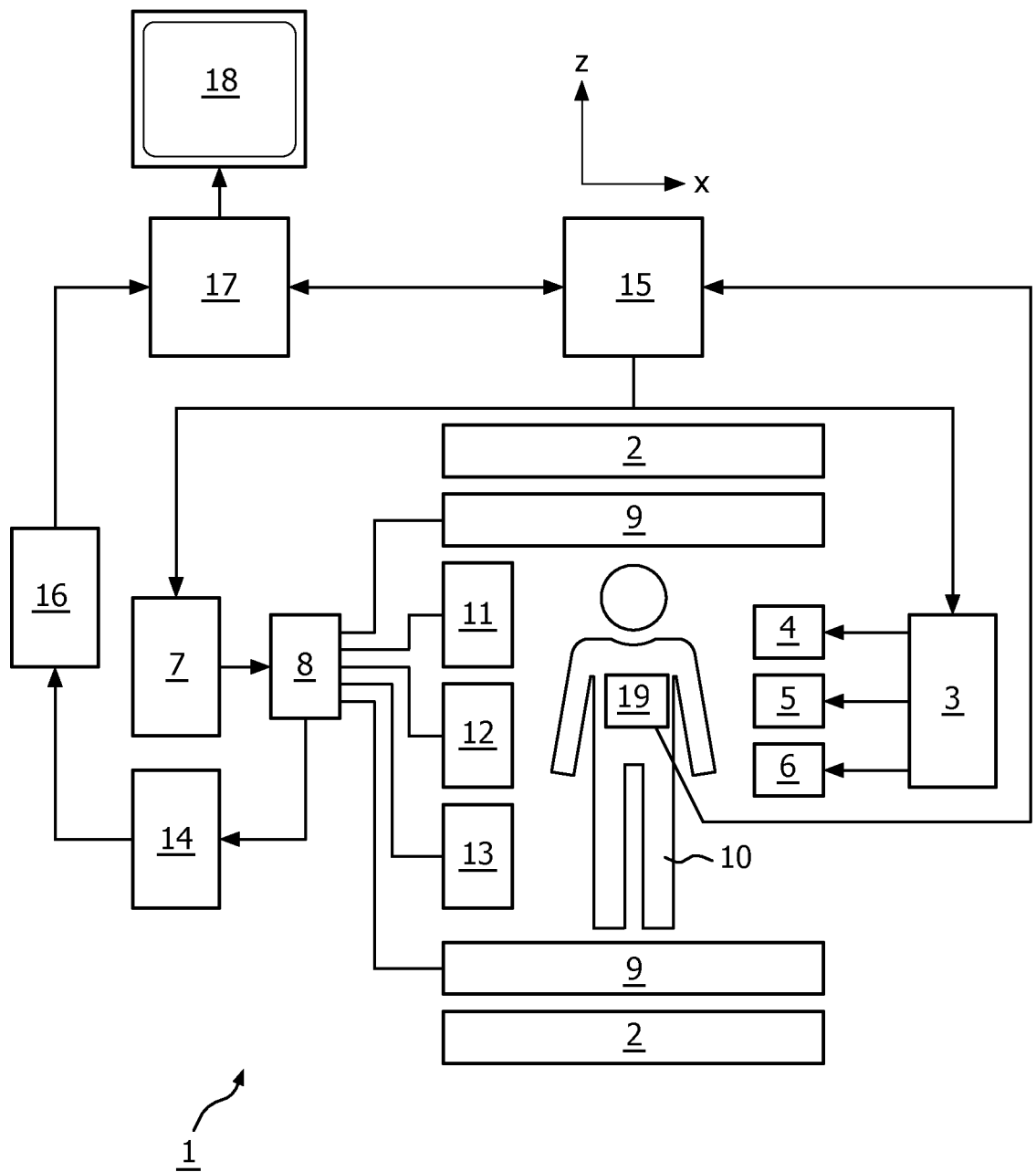
FIG. 1 illustrates a schematic of an MR device according to the invention.

With reference to FIG. 1, an MR imaging system 1 is shown. The system comprises superconducting or resistive main magnet coils 2 such that a substantially uniform, temporarily constant main magnetic field B0 is created along a z-axis through an examination volume.

The magnetic resonance system applies a series of RF pulses and switched magnetic field gradients to invert or excite nuclear magnetic spins, induce magnetic resonance, refocus magnetic resonance, manipulate magnetic resonance, spatially or otherwise encode the magnetic resonance, saturate spins and the like to perform MR imaging.

More specifically, a gradient pulse amplifier 3 applies current pulses to selected ones of whole body gradient coils 4, 5 and 6 along x, y and z-axes of the examination volume. An RF transmitter 7 transmits RF pulses or pulse packets, via a send/receive switch 8 to an RF antenna 9 to transmit RF pulses into the examination volume. A typical MR imaging sequence is composed of a packet of RF pulse sequences of short duration which taken together with each other and any applied magnetic field gradients achieve a selected manipulation of nuclear magnetic resonance. The RF pulses are used to saturate, excite resonance, invert magnetization, refocus resonance, or manipulate resonance and select a portion of a body 10 positioned in the examination volume. The MR signals may also be picked up by the RF antenna 9.

For generation of MR images of limited regions of the body or in general object 10, for example by means of parallel imaging, a set of local array RF coils 11, 12 and 13 are placed contiguous to the region selected for imaging. The array coils 11,12 and 13 can be used to receive MR signals induced by RF transmissions effected via the RF antenna. However, it is also possible to use the array coils 11,12 and 13 to transmit RF signals to the examination volume.

The resultant MR signals are picked up by the RF antenna 9 and/or by the array of RF coils 11,12 and 13 and are demodulated by a receiver 14 preferably including a preamplifier (not shown). The receiver 14 is connected to the RF coils 9, 11, 12 and 13 via a send/receive switch 8.

A host computer 15 controls the gradient pulse amplifier 3 and the transmitter 7 to generate any of a plurality of imaging sequences, such as echo planar imaging (EPI), echo volume imaging, gradient and spin echo imaging, fast spin echo imaging, imaging using ultra-short echo time acquisition pulse sequences and the like.

For the selected sequence, the receiver 14 receives a single or a plurality of MR data lines in a rapid succession following each RF excitation pulse. A data acquisition system 16 performs analogue to digital conversion of the received signals and converts each MR data line to a digital format suitable for further processing. In modern MR devices the data acquisition system 16 is a separate computer which is specialized in acquisition of raw image data.

Ultimately, the digital raw image data is reconstructed into an image representation by a reconstruction processor 17 which applies a Fourier transform or other appropriate reconstruction algorithms. The MR image may represent a planar slice through the patient, an array of parallel planar slices, a three-dimensional volume or the like. The image is then stored in an image memory where it may be accessed for converting slices or other portions of the image representation into appropriate formats for visualization, for example via a video monitor 18 which provides a man readable display of the resultant MR image.

Further shown in FIG. 1 is a respiratory sensor 19 configured to monitor the breath hold level of the patient 10. The respiratory sensor 19 may for example comprise a respiratory belt which provides a motion signal to the host computer 15. Thereupon, the host computer 15 is able to analyze the monitored breath hold level and to provide respective breath hold instructions to the patient 10. These instructions may be provided to the patient either by means of commands spoken by an automated voice provided by the host computer 15 or via a display graphically instructing the patient to perform various actions with respect to holding his breath.

Figure 2:
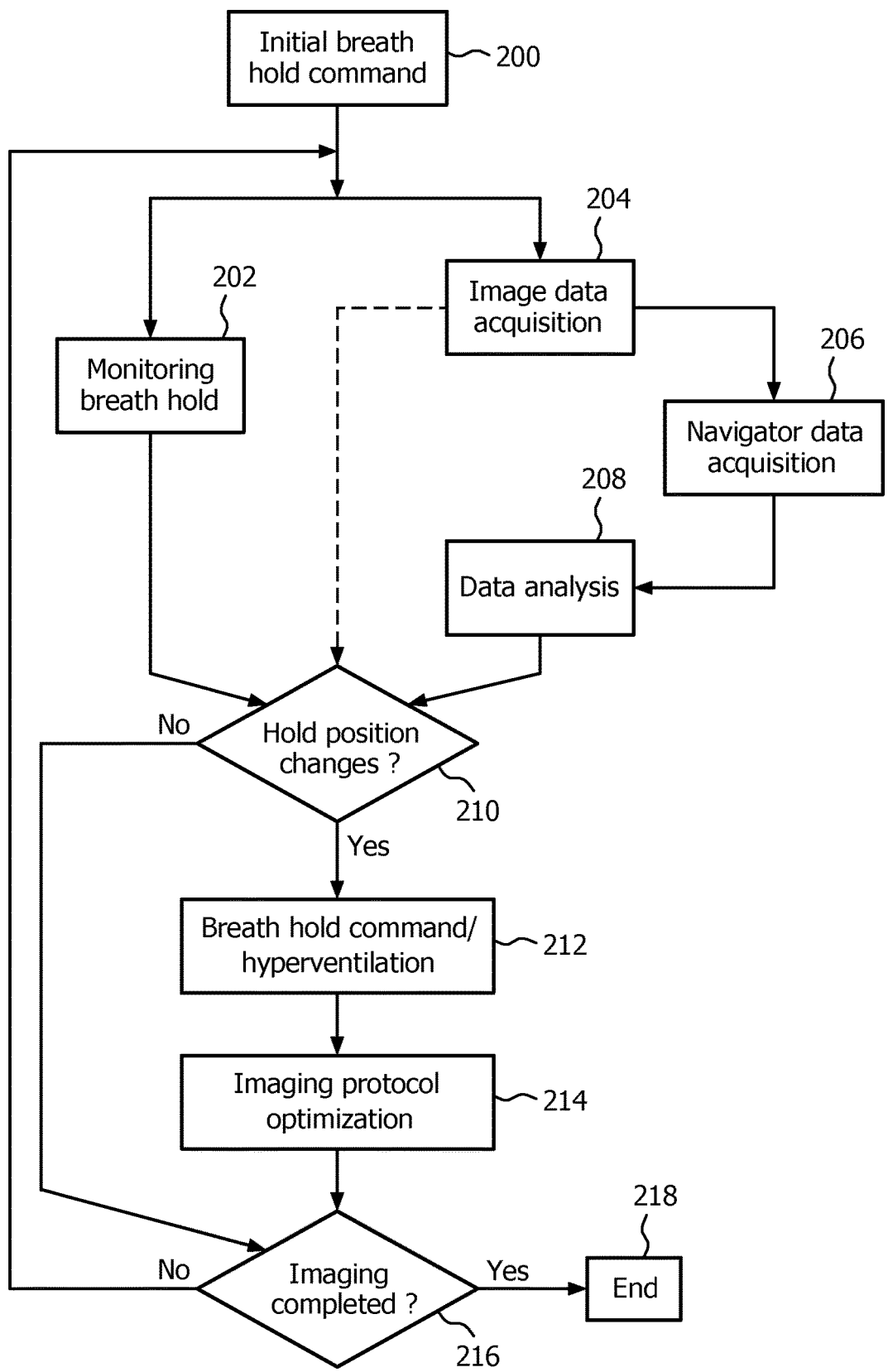
FIG. 2 illustrates a flowchart in accordance with the method described above.

FIG. 2 is a flowchart illustrating an embodiment of the method according to the invention.

The method starts in step 200 with the provision of an initial breath hold command to the patient. Like all breath hold commands, this command may be provided in an automated manner by the MR system to the patient. For this purpose, either pre-recorded voice commands may be used which are played back to the patient, or a synthetically generated voice may be used for that purpose.

The initial breath hold command may comprise a single command informing the patient that he has to hold his breath immediately. However, it is preferred that step 200 comprises a multitude of preparatory steps for acquiring statistics on the patient's breath hold capabilities including performing breath hold tests in an automated manner with the patient. This permits to obtain statistics on the patient's breath hold capabilities and to select and appropriate imaging protocol adapted to said breath hold capabilities.

Step 200 is followed by performing preferably in parallel steps 202 and steps 204-208. In step 202 the breath hold is monitored using for example the respiratory belt 19 of FIG. 1, wherein at the same time in step 204 an MR image data acquisition is performed. Further, an optional navigator data acquisition step 206 may be used which also allows to continuously monitor the breath hold by interleaving the actual data acquisition of step 204 with the navigator acquisition. The navigator data acquired in step 206 and/or the respiratory belt data is then analyzed in step 208. After performing steps 202 and 204 the monitored breath hold level of the patient is analyzed. In case in step 210 it is determined that the hold position did not change during the image data acquisition or that the hold position only changed within small predetermined threshold levels, the method may continue with step 216 in which it is determined if the imaging scan is completed. If this is the case, the image acquired in step 204 is reconstructed for the provision of a final MR image, wherein thereafter in step 218 the method terminates.

In contrast, in case in step 210 it is determined from analysis of the monitored breath hold level acquired in step 202 and/or from navigator data analysis in step 208 that the breath hold level changed above or below a predetermined threshold limit, the method continues with step 212 in which, in an automated manner, a respective breath hold command or hyperventilation command is provided to the patient. As mentioned above, these commands may for example comprise breath in or breath out command timings and/or 'stop breathing' or 'please hold' commands and also patient motivation commands for keeping the actual breath hold level.

As a consequence, in case that a breath is held and the breathing position drifts during the scan phase, a short 'please hold' reminds the patient to further hold his breath and not to 'drift away'. A 'countdown' teller or visual stimulations also can help to motivate the patient to extend his breath hold capabilities.

Step 214 comprising the imaging protocol optimization is an optional step which should be applied in case the motion control detects that a patient cannot follow the breath hold instructions or cannot follow the breath hold for a specified time not fulfilling a specified breath hold capability criteria. In this case, the actually selected imaging protocol can be changed to a new imaging protocol which requires a shorter data acquisition time for completing a respective magnetic resonance imaging scan.

Further, step 214 may be used to make minor changes to the imaging protocol including for example adaptions to slice positions on basis of the navigator scan of step 206.

The method then continues with step 216 in which it is determined if the imaging scan is completed. In case in step 210 it was determined that the breath hold level changed, this typically should not be a case such that thereupon the method continues with the repeated parallel execution of steps 202 and 204, as discussed above.

In contrast, in case a successful breath hold was monitored, the imaging scan will be determined to be completed in step 216, such that the method can thereupon end in step 218 after having performed a reconstruction of the MR image data acquired in the previous step 204.

It has to be noted, that the breathing history of the patient may also be analyzed in order to determine the capability to hold the breath after an automatic breath hold command has been given including the breath hold lengths and drifts during a breath hold. Such an analysis is preferably performed after step 204 and prior to step 210.

Even though the above embodiments were described tailored to physiological motion due to breathing, this concept may be extended to any kinds of physiological motion of the patient like cardiac activity or motion of extremities of the patient.

The invention claimed is:

1. A magnetic resonance imaging system for performing a magnetic resonance imaging scan adaptively optimized to an imaged subject, the system comprising:
   a sensor configured to sense a physiological signal of the subject;
   a speaker configured to provide pre-recorded or synthesized instructions to the subject; and
   a processor configured to:
      analyze the sensed physiological signal to determine instructions to guide the subject to maintain a preferred physiological condition;
      dynamically control the speaker to deliver the pre-recorded or synthesized instructions to the subject to enter or maintain the preferred physiological condition;
      determine an ability of the subject to maintain the preferred physiological condition;
      dynamically change a scan protocol based on the ability of the subject to maintain the preferred physiological condition; and
      control the magnetic resonance imaging scan according to the changed scan protocol.

2. The magnetic resonance imaging system of claim 1, wherein the sensor comprises a respiratory sensor configured to monitor a breath hold level of the subject and wherein the processor is configured to change the scan protocol based on the determined ability of the patient to maintain a selected breathhold level.

3. The magnetic resonance imaging system of claim 1, wherein the sensor comprises a respiratory belt attached to the subject for providing a motion signal to the processor.

4. The magnetic resonance imaging system of claim 2, wherein the processor is further configured to, during imaging:
   determine that the subject is not holding a breath for the desired time; and
   in response to the determination, automatically change the scan protocol to a reduced breath hold scan protocol to perform a remaining portion of the magnetic resonance imaging scan at a reduced resolution scan.

5. The magnetic resonance imaging system of claim 1, wherein the physiological signal is indicative of cardiac activity of the subject.

6. The magnetic resonance imaging system of claim 1, wherein the physiological signal is indicative of motion of the subject.

7. The magnetic resonance imaging system according to claim 5, wherein the processor is further configured to:
   provide control instructions to an air conditioning system to adjust ambient air conditions.

8. The magnetic resonance imaging system of claim 2, wherein the processor is further configured to:
   determine an initial scan protocol based on the breathing history statistics.

9. The magnetic resonance imaging system of claim 2, wherein the processor is further configured to:
   prior to initiating an initial magnetic resonance imaging scan, control the speaker to emulate acoustically radiant noises experienced by a subject during a magnetic resonance scan.

10. A magnetic resonance imaging system for adaptively performing a magnetic resonance imaging scan optimized to an imaged subject, the system comprising:
    a sensor configured to sense breathing of a subject and generate a physiological signal indicative of breathing motion of the subject;
    a speaker configured to acoustically deliver information to the subject during magnetic resonance imaging; and
    a processor configured to:
       prior to imaging the subject, controlling the speaker to emulate acoustic sounds of a magnetic resonance imaging scan and deliver breathhold instructions to the subject and concurrently analyze the physiological signal to determine an ability of the subject to maintain a breathhold;
       based on the determined ability of the patient to maintain a breathhold, selecting an initial scan protocol;
       control a magnetic resonance imager to implement the magnetic resonance imaging using the initial scanned protocol;
       during the magnetic resonance imaging, controlling the speaker to deliver pre-recorded or synthesized instructions to the subject to commence a breathhold and to deliver pre-recorded or synthesized messages to the subject encouraging the subject to maintain the breathhold, and providing pre-recorded or synthesized instructions to the subject to release the breathhold;
       during the scan, monitoring the physiological signal to reassess the ability of the subject to maintain the breathholds;
       in response to a change in the ability of the subject to maintain the breathhold, selecting a new scan protocol based on the changed ability; and
       controlling the magnetic resonance scanner to continue imaging the subject with the new scanned protocol.

* * * * *